(12) United States Patent
Chen et al.

(10) Patent No.: US 9,637,448 B2
(45) Date of Patent: May 2, 2017

(54) RESVERATROL SELENIDE PREPARATION FOR TREATING CANCER

(71) Applicant: Shanghai Ai Qi Ecological Technology Co., Ltd., Shanghai (CN)

(72) Inventors: Gong Chen, Shanghai (CN); Kunyuan Song, Shanghai (CN)

(73) Assignee: Shanghai Ai Qi Ecological Technology Co., Ltd., Shanghai (CN)

( * ) Notice: Subject to any disclaimer, the term of this patent is extended or adjusted under 35 U.S.C. 154(b) by 146 days.

(21) Appl. No.: 14/361,110

(22) PCT Filed: Mar. 28, 2014

(86) PCT No.: PCT/CN2014/074242
§ 371 (c)(1),
(2) Date: May 28, 2014

(87) PCT Pub. No.: WO2015/131423
PCT Pub. Date: Sep. 11, 2015

(65) Prior Publication Data
US 2016/0068481 A1    Mar. 10, 2016

(30) Foreign Application Priority Data
Mar. 6, 2014 (CN) .......................... 2014 1 0080996

(51) Int. Cl.
C07C 391/02    (2006.01)
A61K 31/095    (2006.01)
C07C 51/295    (2006.01)

(52) U.S. Cl.
CPC .......... *C07C 391/02* (2013.01); *A61K 31/095* (2013.01); *C07C 51/295* (2013.01)

(58) Field of Classification Search
None
See application file for complete search history.

(56) References Cited

FOREIGN PATENT DOCUMENTS

CN    101148445 A  *  3/2008 ........... C07D 345/00

OTHER PUBLICATIONS

MedicineNet.com. (2004). Web. <http://www.medterms.com>.*
Bishayee, Anupam. Cancer Prev Res 2009 2(5) 409-418).*
Carter, Lindsay. Endocrine-Related Cancer (2014) 21, R209-R225.*

* cited by examiner

*Primary Examiner* — Golam M M Shameem
*Assistant Examiner* — Laura Daniel

(57) ABSTRACT

A trans-resveratrol selenide for treating cancer has such a structure as:

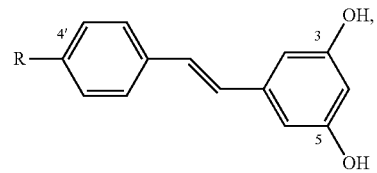

wherein hydroxyls at position 3, 4 and 5 are replaceable, at least one hydroxyl at position 3, 4, 5 is replaced with R, R is alkali metal ion and selenium coordination complex, and

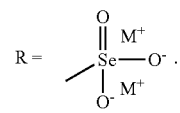

The trans-resveratrol selenide preparation is able to treat various cancers, such as lung cancer, lymphoma, stomach cancer, liver cancer, small intestine cancer, colorectal cancer and gynecologic cancer, and has a good curative effect.

6 Claims, 1 Drawing Sheet

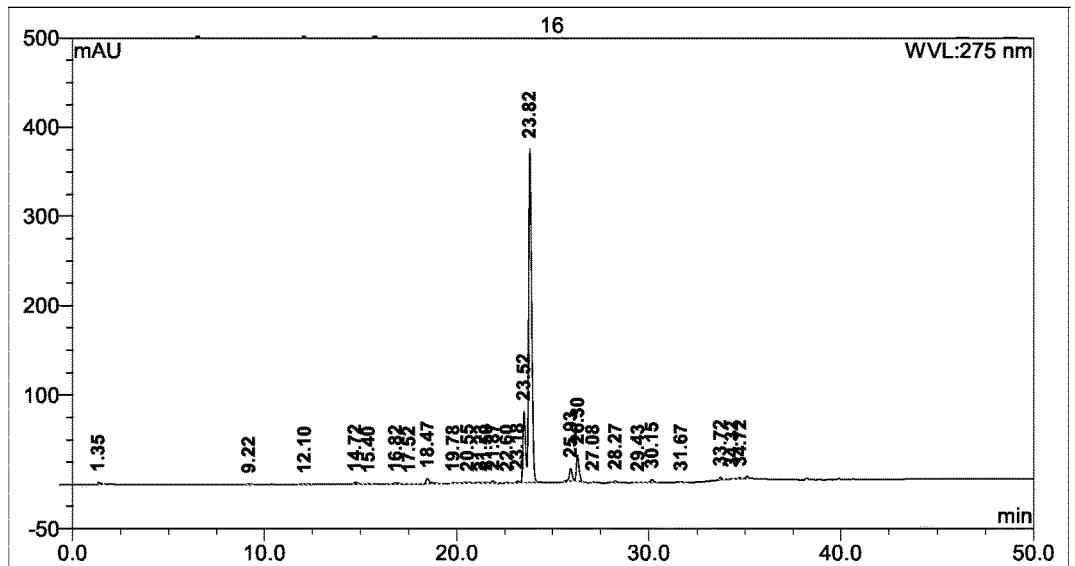
| No. | Ret.Time min | Height mAU | Area mAU*min | Rel.Area % |
|---|---|---|---|---|
| 1 | 1.35 | 2.499 | 0.455 | 0.482 |
| 2 | 9.22 | 0.349 | 0.074 | 0.078 |
| 3 | 12.10 | 0.290 | 0.082 | 0.087 |
| 4 | 14.72 | 2.247 | 0.464 | 0.492 |
| 5 | 15.40 | 0.454 | 0.158 | 0.167 |
| 6 | 16.82 | 1.550 | 0.421 | 0.446 |
| 7 | 17.52 | 0.223 | 0.055 | 0.058 |
| 8 | 18.47 | 5.725 | 1.510 | 1.600 |
| 9 | 19.78 | 0.803 | 0.121 | 0.128 |
| 10 | 20.55 | 0.500 | 0.231 | 0.244 |
| 11 | 21.23 | 0.625 | 0.163 | 0.173 |
| 12 | 21.50 | 0.965 | 0.201 | 0.213 |
| 13 | 21.87 | 2.184 | 0.402 | 0.426 |
| 14 | 22.60 | 1.037 | 0.193 | 0.204 |
| 15 | 23.18 | 2.094 | 0.373 | 0.396 |
| 16 | 23.52 | 69.514 | 9.514 | 10.081 |
| 17 | 23.82 | 373.044 | 70.989 | 75.221 |
| 18 | 25.93 | 13.922 | 2.687 | 2.847 |
| 19 | 26.30 | 28.857 | 4.698 | 4.979 |
| 20 | 27.08 | 0.554 | 0.090 | 0.095 |
| 21 | 28.27 | 1.586 | 0.243 | 0.258 |
| 22 | 29.43 | 0.274 | 0.058 | 0.061 |
| 23 | 30.15 | 2.952 | 0.594 | 0.630 |
| 24 | 31.67 | 0.363 | 0.071 | 0.075 |
| 25 | 33.72 | 2.833 | 0.329 | 0.349 |
| 26 | 34.32 | 0.505 | 0.059 | 0.062 |
| 27 | 34.72 | 1.505 | 0.140 | 0.149 |
| Total: | | 517.455 | 94.374 | 100.00 |

RESVERATROL SELENIDE PREPARATION FOR TREATING CANCER

CROSS REFERENCE OF RELATED APPLICATION

This is a U.S. National Stage under 35 U.S.C 371 of the International Application PCT/CN2014/074242, filed Mar. 28, 2014, which claims priority under 35 U.S.C. 119(a-d) to CN 201410080996.1, filed Mar. 6, 2014.

BACKGROUND OF THE PRESENT INVENTION

Field of Invention

The present invention relates to a medicine for treating cancer, and more particularly to a resveratrol selenide preparation for treating cancer, which has a functional group of alkali metal ion and selenium coordination complex.

Description of Related Arts

Cancer poses a serious threat to human's health and life. According to the statistics of the World Health Organization, about 5 million patients die of cancer every year over the world. Medication is one of the effective therapies for treating cancers. At present, a variety of medicines having positive effect on cancers have been developed, but the curative effect is unsatisfactory. Currently, there are few medicines which have wide curative effects on various cancers. Therefore, developing a medicine having good curative effect on cancer, especially various cancers, has become the focus and nodus of the research.

Trans-resveratrol, which has a higher activity than cis-resveratrol, is a well-known functional polyphenolic compound mainly derived from grape (red wine), polygonum cuspidatum, peanut, mulberry, etc. It is a natural polyphenol with strong biological characteristics. The resveratrol selenide preparation fortified by selenium has many biological functions of selenium compound, and it has no toxicity or side effect at high doses. Hence, it is a valuable organic selenium compound.

Resveratrol is originally used as chemical preventive agent against cancer, platelet aggregation, atherosclerosis and cardiovascular disease over the world. A research by United States Department of Agriculture indicated that peanut skin and peanut kernel contain plenty of resveratrol. Many experiments and researches have proved that resveratrol has beneficial effects on cardiovascular diseases and cancers, and also has an obvious preventive effect on hormone-dependent tumors, osteoporosis, acne, and Alzheimer's disease. Moreover, it has antiviral and immune adjustment function. Besides, resveratrol is able to work on a monomeric anti-aging enzyme in human body, so that it plays a potential role in preventing diseases of all age groups and prolonging life expectancy.

However, it is reported that traditional resveratrol has selectivity and limitation in treating cancers, referring to "Cancer-specific Therapeutic Potential of Resveratrol: Metabolic Approach against Hallmarks of Cancer" (http://functionalfoodscenter.net/files/73514409.pdf). In addition, other researches indicated that the resveratrol could be ineffective in inhibiting tumor growth in certain animal models despite its in vitro antitumor action in related cells, referring to "Cancer prevention and treatment with resveratrol: from rodent studies to clinical trials, Cancer Prev Res May 2009 2; 409".

SUMMARY OF THE PRESENT INVENTION

An object of the present invention is to provide a resveratrol selenide preparation which is able to target cancer cells effectively and has a functional group of alkali metal ion and selenium coordination complex.

A resveratrol selenide for treating cancer has such a structure as:

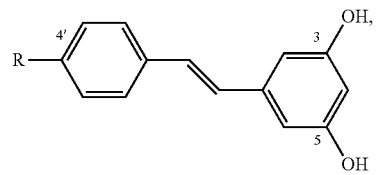

wherein hydroxyls at position 3, 4 and 5 are replaceable, at least one hydroxyl at position 3, 4, 5 is replaced with R, R is alkali metal ion and selenium coordination complex, and

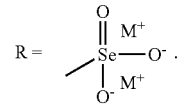

A method for preparing the resveratrol selenide for treating cancer, comprises following steps of:

a) reacting trans-resveratrol with at least one inorganic metallic alkali, to obtain resveratrol hydroxy acid salt; and b) reacting the resveratrol hydroxy acid salt with $SeO_2$, to obtain preparation of the trans-resveratrol selenide, which has a functional group of alkali metal ion and selenium coordination complex.

Preferably, the inorganic metallic alkali in step a) is sodium hydroxide, potassium hydroxide, or magnesium hydroxide.

Preferably, a reaction temperature in step a) is 80° C.~150° C., and a reaction temperature in step b) is 120° C.~360° C.

Preferably, a purity of the trans-resveratrol in step a) is not less than 99%.

Preferably, the preparation of the trans-resveratrol selenide obtained in step b), which has the functional group of alkali metal ion and selenium coordination complex, comprises trans-resveratrol selenide accounting for not less than 80% (mass fraction), cis-resveratrol selenide accounting for not more than 8%, and highly purified resveratrol accounting for not less than 10%, wherein a purity of the highly purified resveratrol is not less than 99%.

The resveratrol selenide can be applied in treating cancers.

Benefits of the present invention are as follows. The resveratrol selenide preparation in the present invention has groundbreaking effect in aspect of killing cancer cells and increasing immunity of body. It is able to treat various cancers, such as lung cancer, lymphoma, stomach cancer, liver cancer, small intestine cancer, colorectal cancer and gynecologic cancer, and has a good curative effect.

These and other objectives, features, and advantages of the present invention will become apparent from the following detailed description, the accompanying drawings, and the appended claims.

BRIEF DESCRIPTION OF THE DRAWINGS

The FIGURE is a high performance liquid chromatogram of resveratrol selenide having a functional group of alkali metal ion and selenium coordination complex which is obtained according to a preferred embodiment of the present invention.

DETAILED DESCRIPTION OF THE PREFERRED EMBODIMENT

According to a preferred embodiment of the present invention, a trans-resveratrol selenide preparation for treating cancer has resveratrol hydroxy acid and a functional group of alkali metal ion and selenium coordination complex.

According to another preferred embodiment of the present invention, a method for preparing a trans-resveratrol selenide preparation, which has a functional group of alkali metal ion and selenium coordination complex, comprises following steps of:

a) reacting trans-resveratrol having a purity of not less than 99% with at least one inorganic metallic alkali, to obtain resveratrol hydroxy acid salt; and b) reacting the resveratrol hydroxy acid salt with $SeO_2$, to obtain the trans-resveratrol selenide and cis-resveratrol selenide, which have the functional groups of alkali metal ion and selenium coordination complex, i.e., selenium-enriched compound preparation of trans-resveratrol selenide having the functional groups of alkali metal ion and selenium coordination complex.

Preferably, the compound preparation of resveratrol selenide comprises: trans-resveratrol selenide accounting for not less than 80% (mass fraction), cis-resveratrol selenide accounting for not more than 8%, and highly purified resveratrol accounting for not less than 10%, wherein a purity of the highly purified resveratrol is not less than 99%;

The cis-resveratrol has such a structure as:

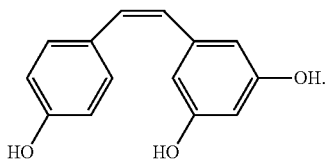 [SMILES: Oc1ccc(/C=C\c2cc(O)cc(O)c2)cc1]

The cis-resveratrol selenide has such a structure as:

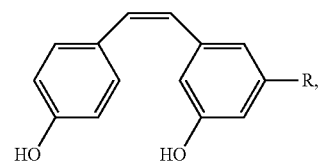

wherein the functional group of alkali metal ion and selenium coordination complex

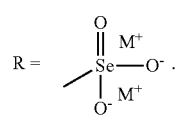

According to another preferred embodiment of the present invention, the trans-resveratrol used as substrate has a higher activity than cis-resveratrol. The trans-resveratrol selenide preparation has the functional group of alkali metal ion and selenium coordination complex.

The trans-resveratrol has such a structure as:

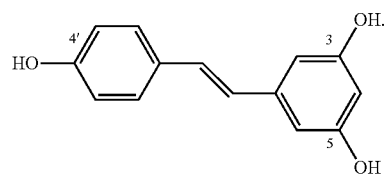 [SMILES: Oc1ccc(/C=C/c2cc(O)cc(O)c2)cc1]

After the selenylation of the trans-resveratrol $C_{14}H_{12}O_3$ having a molecular weight of 228.25, the trans-resveratrol selenide is obtained, which has such a structure as:

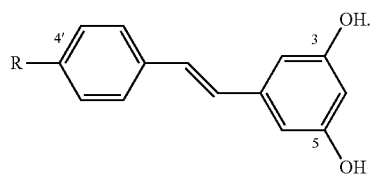

The functional group of alkali metal ion and selenium coordination complex

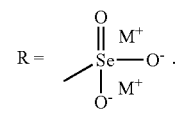

Note: R could be at position 3, 4, or 5. With the increase of the selenium content in the synthesizing process of trans-resveratrol selenide, the synthesis reaction becomes more and more intensive, and the reaction activity increases. Any two of the positions 3, 4, and 5 could be conjugated with R at the same time. For example, position 3 and 4, position 4 and 5, or position 3 and 5, which varies according to the PH value of the product. The trans-resveratrol selenide herein has a selenium content of 36.6%.

The functional group of alkali metal ion and selenium coordination complex

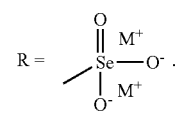

EXAMPLE 1 a) reacting trans-resveratrol having a purity of not less than 99% with sodium hydroxide, to obtain resveratrol hydroxy acid sodium, wherein trans-resveratrol:sodium hydroxide=1:0.25 (mass ratio), a reaction temperature is 120° C., and a reaction time is 180 s; and b) reacting the resveratrol hydroxy acid sodium with $SeO_2$, to obtain the trans-resveratrol selenide preparation, which has a mass fraction of not less than 80% and has a functional group of alkali metal ion and selenium coordination complex, and cis-resveratrol selenide preparation, which has a mass fraction of not more than 8%, wherein resveratrol hydroxy acid sodium:$SeO_2$=1:0.35, a reaction temperature is 280° C., and a reaction time is 250 s. After cooling, selenium-enriched compound preparation of trans-resveratrol selenide having the functional groups of alkali metal ion and selenium coordination complex is obtained.

In the final product, the compound preparation of resveratrol selenide comprises trans-resveratrol selenide having a mass fraction of not less than 80%, cis-resveratrol selenide having a mass fraction of not more than 8%, and highly purified resveratrol having a mass fraction of not less than 10%, wherein a purity of the highly purified resveratrol is not less than 99%.

EXAMPLE 2 a) reacting trans-resveratrol having a purity of not less than 99% with potassium hydroxide, to obtain resveratrol hydroxy acid potassium, wherein trans-resveratrol:potassium hydroxide=1:0.25 (mass ratio), a reaction temperature is 120° C., and a reaction time is 180 s; and b) reacting the resveratrol hydroxy acid potassium with $SeO_2$, to obtain the trans-resveratrol selenide preparation, which has a mass fraction of not less than 80% and has a functional group of alkali metal ion and selenium coordination complex, and cis-resveratrol selenide preparation, which has a mass fraction of not more than 8%, wherein resveratrol hydroxy sodium:$SeO_2$=1:0.35 (mass ratio), a reaction temperature is 280° C., and a reaction time is 250 s. After cooling, selenium-enriched compound preparation of trans-resveratrol selenide having the functional groups of alkali metal ion and selenium coordination complex is obtained.

In the final product, the compound preparation of resveratrol selenide comprises trans-resveratrol selenide having a mass fraction of not less than 80%, cis-resveratrol selenide having a mass fraction of not more than 8%, and highly purified resveratrol having a mass fraction of not less than 10%, wherein a purity of the highly purified resveratrol is not less than 99%.

EXAMPLE 3 a) reacting trans-resveratrol having a purity of not less than 99% with magnesium hydroxide, to obtain resveratrol hydroxy acid magnesium, wherein trans-resveratrol:magnesium hydroxide=1:0.25 (mass ratio), a reaction temperature is 120° C., and a reaction time is 180 s; and b) reacting the resveratrol hydroxy acid magnesium with $SeO_2$, to obtain the trans-resveratrol selenide preparation, which has a mass fraction of not less than 80% and has a functional group of alkali metal ion and selenium coordination complex, and cis-resveratrol selenide preparation, which has a mass fraction of not more than 8%, wherein resveratrol hydroxy acid sodium:$SeO_2$=1:0.35 (mass ratio), a reaction temperature is 280° C., and a reaction time is 250 s. After cooling, selenium-enriched compound preparation of trans-resveratrol selenide having the functional groups of alkali metal ion and selenium coordination complex is obtained.

In the final product, the compound preparation of resveratrol selenide comprises trans-resveratrol selenide having a mass fraction of not less than 80%, cis-resveratrol selenide having a mass fraction of not more than 8%, and highly purified resveratrol having a mass fraction of not less than 10%, wherein a purity of the highly purified resveratrol is not less than 99%.

The treating effects of the medicine on different volunteers

Case 1:

Volunteer 1 Gender: Female Age: 58

The volunteer took the resveratrol selenide preparation twice a day, morning and evening, and took 0.4 g each time, wherein the resveratrol selenide was prepared according to Example 1 of the present invention.

CT Contrast-enhanced Chest CT Scan Report (Before taking medicine)

Report date: 2012 Aug. 31

Clinical information: The left lung adenocarcinoma with squamoid differentiation Examination Method and Part Imaging Manifestations 1. The lump on the hilum of the left lung had an unclear boundary with the atelectasis, and the lump of the hilum swelling outward had a size of 32×19 mm (IM27).

2. 5 groups of mediastinal lymph-nodes had lymphadenectasis, and the size was 23×14 mm (IM15).

3. Multiple periventricular low-density lesions (PVLD) and a cyst were found in the liver.

Ultrasonic examination report (After taking medicine)

Report date: 2012 Nov. 12

Imaging manifestations: (Compared with 2012 Aug. 31)

1. The lump on the hilum of the left lung had a clear boundary with atelectasis, and the size of the lump of the hilum swelling outward was decreased to 11×6 mm (IM27).

2. 5 groups of mediastinal lymph-nodes had lymphadenectasis, and the size was 23×14 mm (IM15).

3. There were no multiple periventricular low-density lesions (PVLD) in the liver, and the cyst disappeared.

Case 2:

Volunteer 2 Gender: Male Age: 51

The volunteer took the resveratrol selenide preparation twice a day, morning and evening, and took 0.4 g each time, wherein the resveratrol selenide was prepared according to Example 2 of the present invention.

Report date: 2012 Aug. 21 (Before taking medicine)

Radiological manifestations:

Adenocarcinoma of small intestine changed after operation. There was FDG uptake at the anastomotic stoma in the left lower quadrant, and the adenocarcinoma relapsed.

Multiple lymph nodes with increased metabolism were found in the abdominopelvic cavity, and tumor metastasis and progression were considered.

Splenomegaly

Obsolete lesions in two lungs

Diagnose: Adenocarcinoma of small intestine relapsed after the operation, and the tumor metastasized.

Radiology imaging examination report (After taking medicine)

Report date: 2012 Dec. 13

Clinical diagnose: Abdominal multiple tumor after the operation of adenocarcinoma of small intestine Radiological manifestations: (Compared with the examination result of 2012 Aug. 21)

A high-density suture shadow was found at the operation area, and no obvious incrassation or abnormal enhancement at the anastomotic stoma was found.

No lymphadenectasis was found in the abdominopelvic cavity.

No cyst was found in the left lobe of liver.

The size of the splenomegaly was decreased, and the density was normal.

No obsolete lesion on lungs

Radiologic diagnose: The small intestine changed after the operation, and no obvious recurrence or metastasis was found.

Case 3:

Volunteer 3: lymphoma patient Gender: Male Age: 63

The volunteer took the resveratrol selenide preparation twice a day, morning and evening, and took 0.4 g each time, wherein the resveratrol selenide was prepared according to Example 3 of the present invention.

Report date: 2013 Feb. 25 (Before taking medicine)

Clinical diagnose: multiple intracranial space-occupying lesions

Test item: CT

Examination Result:

1. The hypermetabolic nodule in the left thyroid was a primary malignant tumor. Multiple space-occupying lesions were found in the brain and the metabolism was increased, which conformed to the imaging manifestation of the malignant tumor.

2. The lymphadenectasis was found under the bilateral jaws, at the parapharyngeal space, at the jugular vein space, and at the neck root, and the metabolism was partly increased, so metastasis was considered.

3. Nodules were found in the superior and inferior lobe of the right lung.

Report date: 2013 May 15 (After taking medicine)

Examination Result:

1. The brain had normal shape and size. Compared with the former examination result of 2013 Feb. 28, the focus had shrunk, and no obvious abnormal enhancement was found in the rest of the brain.

2. The size of the lymph nodes under the bilateral jaws, at the parapharyngeal space, at the jugular vein space, and at the neck root was decreased.

3. No nodules were found in the superior and inferior lobe of the right lung.

Diagnose: The multiple intracerebral space-occupying lesions had been improved after therapy.

Report date: 2013 May 23 (After taking medicine)

1. The focus had shrunk, and no obvious abnormal enhancement was found in the rest of the brain.

2. The size of the lymph nodes under the bilateral jaws, at the parapharyngeal space, at the jugular vein space, and at the neck root was normal.

3. No nodule was found in the superior and inferior lobe of the right lung.

Diagnose: The patient's condition had obviously improved after taking the medicine.

Case 4:

The volunteer took the resveratrol selenide preparation twice a day, morning and evening, and took 0.4 g each time, wherein the resveratrol selenide was prepared according to Example 1 of the present invention.

Volunteer 4: Gender: Female Age: 57

Clinical diagnose: tumor Examination part and examination name: epigastrium CT, CT reconstruction Report date: 2013 Nov. 13 (Before taking medicine)

Radiological manifestations: Multiple foci of slightly low density and different sizes were found in the liver. The biggest focus had a sectional area of about 97*61 mm. The radiological imaging demonstrated a heterogeneous enhancement.

Radiologic diagnose: Metastatic liver tumor

Report date: 2013 Dec. 16 (After taking medicine)

Radiological manifestations: Most of the multiple foci of slightly low density in the liver disappeared; the biggest sectional area was 51*34 mm.

Radiologic diagnose: Most tumors in the liver disappeared. The remaining tumors decreased in size in comparison with those before taking the medicine.

It is worth mentioning that 100 volunteers have taken the resveratrol selenide preparation for treating cancer in the present invention of certain doses, wherein the 100 volunteers included patients of lung cancer, lymphoma, stomach cancer, liver cancer, small intestine cancer, colorectal cancer and gynecologic cancer. According to the statistics, 84% of the volunteers have been relieved from their cancers, wherein 62% healed, and there was no obvious side effect.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

An acute oral toxicity testing of P13 in rats is described as follows, wherein P13 is resveratrol selenide preparation obtained according to the embodiment 1 of the present invention.

Abstract of Toxicity Test

Object: Observing toxic reaction and deaths of rats after intragastric administration of test sample P13 in them, in order to preliminarily evaluate the safety of the test sample P13

Method: 50 healthy SD rats, selected as the test animals, half male and half female, were randomly divided into 5 groups, i.e., dose group 1 (194 mg/kg), dose group 2 (324 mg/kg), dose group 3 (540 mg/kg), dose group 4 (900 mg/kg), dose group 5 (1500 mg/kg). Each dose group had 10 animals, half male and half female. The night before the dosing day, the rats were not allowed to eat, but allowed to drink. On the dosing day, the rats were intragastrically fed with 1 ml/100 g bw once. Within 4 hours after the intragastric administration, reactions and death of the animals were closely observed. Then the animals were observed twice a day, morning and afternoon, for 14 days to record the status of death and near-death. The death animals were necropsied promptly. Other animals were processed with gross anatomy after the end of the observation period. The gross pathologic change of each animal was recorded.

Result: (1) After the rats were fed with P13 and during the observation period, all of the rats in the dose group 5 died. In the dose group 4, 4 male rats died and all of the female rats died. In the dose group 3, no male rat died and 4 female rats died. In the dose group 2, 1 male rat died and 2 female rats died. In the dose group 1, none of the rats died. All of the other animals survived. (2) The animals were necropsied after the observation period of 14 days, wherein the rats 2200, 2202, 2203, 2302, 1301 and 1302 had symptom of rough liver surface, and other visceral organs had no obvious symptom.

Conclusion: According to *[H] GPT1*-1 *Technical guidelines for acute toxicity testing of chemicals* issued by China Food and Drug Administration (CFDA) and results of pretest, doses were designed and the test were processed. According to the results of the test, median lethal dose ($LD_{50}$) of P13 in this acute oral toxicity testing in male and female SD rat is calculated and listed as follows.

Male rats: 677.58 mg/kg, confidence limit: 449.99~1047 mg/kg

Female rats: 379.96 mg/kg, confidence limit: 252.94~564.88 mg/kg

1. Name of the Testing

Acute oral toxicity testing of P13 in rats

2. Objective of the Testing

Researching median lethal dose ($LD_{50}$) of P13 in acute oral toxicity testing in rats, and providing basis for dose design in subchronic and chronic toxicology research 3. Criterion and Reference The testing was based on *[H] GPT1-1 Technical guidelines for acute toxicity testing of chemicals* issued by China Food and Drug Administration (CFDA).

4. Testing Institution

Testing institution: Shanghai Siper-BK Lab Animal Co. Ltd.

Address: 3577 Jinke Rd., Pudong New District, Shanghai

Postcode: 201203

Telephone: 021-50793648

Fax: (021) 50793645

5. Client and Contact Person

Client: Shanghai Spark Pharmaceutical Co., Ltd. (Shanghai Ai Qi Yi Yao Ji Shu You Xian Gong Si)

Address: Rm. 1110, No. 781, Cailun Rd., Zhangjiang Hi-Tech Park, Shanghai

Contact person: Diwei Song

Mobile: 13386238676

6. Principal of Testing Institution, Principal of Project and Related Personnel of Testing Principal of testing institution: Guoqiang Chen Address: 3577 Jinke Rd. Postcode: 201203

Telephone: 50793648 Email: chenguoqiang@slarc.org.cn

Principal of project: Liya Zhao

Address: 3577 Jinke Rd. Postcode: 201203

Telephone: 50793648 Email: zhaoliya@slarc.org.cn

Principal of rearing management: Yi Jin

Address: 3577 Jinke Rd. Postcode: 201203

Telephone: 50793648 Email: jinyi@slarc.org.cn

Principal of test sample management: Xiaojun Zhu

Telephone: 50793648 Email: zhuxiaojun@slarc.org.cn

Principal of file management: Zhenyu Nan

Telephone: 50793648 Email: nanzhenyu@slarc.org.cn

Personnel giving medicine: Lei Liu

Symptom observer: Wei Li, Yikai Shi, Lei Liu, etc.

7. Quality Assurance

Principle of QAU: Ying Zhao

Address: 3577 Enke Rd. Postcode: 201203

Telephone: 50793648 Email: zhaoying@slarc.org.cn

8. Test Sample and Solvent 8.1 Test Sample

Chinese name: P13

English name: P13

Lot number: 20130903

CAS number: Not provided by the client

Physical property: Solid powder

Purity: Not provided by the client

Provider: Shanghai Spark Pharmaceutical Co., Ltd. (Shanghai Ai Qi Yi Yao Ji Shu You Xian Gong Si)

Providing date: 20130903

Expiry date: 20150903

Total weight: (Including the container weight) 55.497 g

Protective measure: The persons who contact with the test sample should take appropriate protective measures, including masks, hats, gloves, overalls, and etc.

Storage condition: At room temperature

Storage site: Test sample room of the testing institution

Stability: The client confirmed that the test sample was stable at the storage temperature.

Treatment of residual test sample: After the testing, residual test sample was taken back to the test sample room, and treated according to SOP.

8.2 Solvent

Name: ultrapure water

9. Test Schedule

Date of initial test: Sep. 11, 2013

Date of introducing the rats: Sep. 13, 2013

Date of starting the test: Sep. 23, 2013

Date of ending the test: Oct. 7, 2013

Date of draft report: Nov. 1, 2013

Date of final report: Nov. 7, 2013

10. Material and Method 10.1 Test System

Species: Rat

Strain: SD (Sprague Dawley)

Level: SPF, referring to National Standard of People's Republic of China—GB 14922.2-2011 Experimental Animal Microbiology Level Monitoring Provider: Shanghai Sippr-BK Lab Animal Co. Ltd.

Experimental animal production license: SCXK(Shanghai)2008-0016

Experimental animal quality certification: 2008001634592

Choosing reason: The rat is recognized as the preferred animal for this kind of acute toxicity testing. It has stable hereditary feature and distinct background data.

Requirement of animals: Virgin, healthy, and compliant with quality requirements on experimental animals Animal count: total 54, half female and half male; used 50, half female and half male Weight: At the time of introducing, male animals' weight range 100-130 g, female animals' weight range 120-140 g Health examination and adaptation: Within 24 hours after the animals were introduced, the animals were checked-up. The animals having abnormal behavior were eliminated promptly. During the adaptation period, each cage contained 5 animals, which adapted for at least 5 days.

After the adaptation period, 50 rats were selected as the experimental animals of the acute oral toxicity testing in rats. When the dosing was started, the animal weight was 150~180 g.

10.2 Test Condition

Rearing Condition:

The test site was located at layer 2, layer 3 and layer 4 of the rearing rack 2008043-ZYZX in Room 3139, barrier system, No. 3 building of the testing institution. The experimental animal usage license was SYXK(Shanghai)2008-0058. Testing animals were raised in plastic cages. During the adaptation period, the animals were raised in cages having size of L38.00 cm*W32.5 cm*H17.5 cm, which were put on the rearing rack. The rearing rack had 7 layers, each of which comprised 5 cages. The rearing rack had a size of L167.0 cm*W70.0*H171.0 cm. After dosing, each cage contained 5 animals.

The floor of the animal room was wiped with disinfectant every day, and the disinfectant was replaced every week. The cages were replaced once a week. Water was fed in plastic bottles, and the animals drank and ate freely.

Environmental Condition:

The air pressure in the animal room (L6.2 m*W5.8 m*H2.7 m) was kept positive by an air conditioning unit, which took in the fresh air and exhausted air. The temperature was 20~26° C. The relative humidity was 40~70%, except when the room was being cleaned. The illumination was not less than 200 Lux, and the illumination was on for 12 hours and off for 12 hours a day. The noise was not more than 60 dB. Ventilation frequency was not less than 15 times per hour. The falling bacterial count was not more than 3. (When there was no animal, a plate with a diameter of 9 cm was exposed for 30 minutes.)

Ingestion and Drinking:

The animal fodder was the complete nutritional solid fodder, which was provided by Shanghai Sippr-BK Lab Animal Co., Ltd. The fodder was sterilized with high pressure steam before eaten by the experimental animals. The fodder quality testing report was provided, which proved that both the nutritional ingredient and the pollutant content conformed to national standard GB14924.3-2010 Nutritional ingredient of compound feed for experimental animal and GB14924.2-2001 Hygienic standard of compound feed for experimental animal.

The water the animals drunk was the filtered water prepared by the water purification system of the testing institution. The water quality was tested by a professional institution, and the test indices conformed to GB 5749-2006 Hygienic standard for drinking water.

Animal Welfare:

The residual animals after grouping were used in other testings or euthanized. The animals near death in the testing or alive at the end of the testing were euthanized. The euthanasia was embodied as carbon dioxide suffocation. The corpses were disposed by Shanghai Animal Harmless Disposal Center.

10.3 Test Method 10.3.1 Dose Design 5 dose groups were designed, i.e., dose group 1 (194 mg/kg), dose group 2 (324 mg/kg), dose group 3 (540 mg/kg), dose group 4 (900 mg/kg), dose group 5 (1500 mg/kg). The animals of the dose group 1~5 were intragastrically fed with test sample suspension of 19.4 mg/mL, 32.4 mg/mL, 54 mg/mL, 90 mg/mL, and 150 mg/mL, respectively. The intragastric volume was 1 ml/100 g bw, and the animals were exposed once.

The dose was designed based on *[H] GPT1-1 Technical guidelines for acute toxicity testing of chemicals* issued by China Food and Drug Administration (CFDA) and results of the pre-test. In the pre-test, 2 female animals and 2 male animals were orally exposed to the test sample of each dose. The results indicated that all of the 4 animals exposed to the test sample of 1500 mg/kg died; 1 of the animals exposed to the test sample of 400 mg/kg died; and none of the 4 animals exposed to the test sample of 200 mg/kg died. Therefore, 5 doses between 200 mg/kg and 1500 mg/kg were designed for the formal test.

10.3.2 Grouping Animals

The animals were divided into groups after the end of the adaptation period. Grouping method: After the end of the adaptation period, all of the animals were weighed and their average weight was calculated. The animals usually in good condition were selected. The weight difference among the animals of the same gender and in the same dose group was less than 10% of the average weight. The difference of the average weights of the animals of the same gender between any two dose groups was less than 5%. The animals were identified by original codes. The animals were ranked from largest weight to smallest weight, and were divided into groups, wherein each group comprised 5 animals. From each of the five groups, one animal was randomly taken out to form a certain dose group. New codes of the animals were recorded, and they were random and not ranked in ascending or descending order of the weight. The animals were taken out according to the original codes. The corresponding dose groups and new codes were found in the grouping table, and then the animals were put into the corresponding dose groups in turn.

Animal identification: The animals were identified by cage cards, picric acid hair dye, and ear tag. The cage card showed the code and the dose group of the animal. The hair identification showed the units digit of the animal code in one group, i.e. 0~9. The ear tag showed the units digit of the animal code in one group, i.e. 0~9, and the group number. The dose design and animal dose groups are shown in Table 1.

TABLE 1

Dose design and animal dose groups

| Group | Dose (mg/kg diet) | Gender | Amount | Animal code |
|---|---|---|---|---|
| Dose group 1 | 194 | ♂ | 5 | 1100-1104 |
| Dose group 2 | 324 | ♂ | 5 | 1200-1204 |
| Dose group 3 | 540 | ♂ | 5 | 1300-1304 |
| Dose group 4 | 900 | ♂ | 5 | 1400-1404 |
| Dose group 5 | 1500 | ♂ | 5 | 1500-1504 |
| Dose group 1 | 194 | ♀ | 5 | 2100-2104 |
| Dose group 2 | 324 | ♀ | 5 | 2200-2204 |
| Dose group 3 | 540 | ♀ | 5 | 2300-2304 |
| Dose group 4 | 900 | ♀ | 5 | 2400-2404 |
| Dose group 5 | 1500 | ♀ | 5 | 2500-2504 |

10.3.3 Preparation of Test Sample

The scale 40 mL was calibrated on the blue cap reagent bottle with pure water for standby application.

The test sample was prepared on the exposure day. The theoretical sample weights were calculated according to the dose design, and the test samples were respectively weighed out and put into the calibrated blue cap reagent bottles. Little ultrapure water was added and stirred evenly, and then the volume of the solution was adjusted to the calibrated scale. After the preparation, the blue cap reagent bottles were labeled for standby application. The calculating formulas were as follows. Concentration of test sample (mg/mL)= Dose (mg/kg)/Intragastric volume (mL/kg). Theoretical sample weight (mg)=Preparation volume (mL)*Concentration of test sample (mg/mL).

TABLE 2

Concentration of test sample

| Group | Dose (mg/kg bw) | Intragastric volume (mL/kg bw) | Sample concentration (mg/mL) | Theoretical sample weight (g) | Metered volume (mL) |
|---|---|---|---|---|---|
| Dose group 1 | 194 | 10 | 19.4 | 0.776 | 40 |
| Dose group 2 | 324 | 10 | 32.4 | 1.296 | 40 |
| Dose group 3 | 540 | 10 | 54 | 2.16 | 40 |
| Dose group 4 | 900 | 10 | 90 | 3.6 | 40 |
| Dose group 5 | 1500 | 10 | 150 | 6 | 40 |

10.3.4 Exposure Routes, Exposure Cycle, and Observation Period

Based on the probable routes through which human beings may be exposed to the test sample, the animals were orally exposed to the test sample by intragastric administration. The prepared test sample was stirred with a magnetic stirring rod for 5 minutes, and then the dosing was started. The test sample was being stirred during the dosing. The dosing volume was equal to 10 mL/kg*weight. Before the dosing, the animals were weighed, and the dosing volume was calculated. The intragastric administration was processed with disposable sterile syringes having range of 5 mL, minimum scale of 0.2 mL, and syringe needle of 16G. The animals were dosed with test sample suspension of certain concentration. The animals were dosed at the grouping day. The night before the dosing day, the animals were not allowed to eat, but allowed to drink. 2 hours after intragastric administration, the animals resumed feeding. The animals were exposed to the test sample once. The observation period lasted for 14 days. When all symptoms disappeared, the test ended. The observation period could be extended to 21 days or 28 days when necessary. When the test ended, the animals in dose group 1, dose group 2, dose group 3, dose group 4 and dose group 5 were processed with gross anatomy according to the codes of animals anatomized as planned after exposure (shown in Table 3).

TABLE 3

Code of animal anatomised as planned

| Group | Gender | Animal code |
|---|---|---|
| Dose group 1 | ♂ | 1100-1104 |
| Dose group 2 | ♂ | 1200-1204 |
| Dose group 3 | ♂ | 1300-1304 |
| Dose group 4 | ♂ | 1400-1404 |
| Dose group 5 | ♂ | 1500-1504 |
| Dose group 1 | ♀ | 2100-2104 |
| Dose group 2 | ♀ | 2200-2204 |
| Dose group 3 | ♀ | 2300-2304 |
| Dose group 4 | ♀ | 2400-2404 |
| Dose group 5 | ♀ | 2500-2504 |

10.3.5 Clinical Observation and Examination

1) Symptoms Observation

Within 4 hours after the dosing, the animals were closely observed. From the $1^{st}$ day to the $14^{th}$ day after the dosing, the animals were observed once a day to record symptoms, wherein the dosing day was the $0^{th}$ day. The animals were observed to record the changes of skin and hair, eyes, mucous membranes, respiratory system, circulatory system and nervous system, especially the changes of physical activity and behavior. Toxic symptoms of the animals, and its occurrence, remission and disappearance time were recorded. When the animals died, the death time was recorded.

The animals were observed twice a day, morning and afternoon, to record the number of death and near-death.

2) Weighing

The animal was weighed once on the dosing day. During the observation period, the animals were weighed once every 3 days.

3) Gross Anatomy

All animals should be processed with gross anatomy. During the test, the animals executed because of near-death, and dead animals were processed with gross anatomy promptly. Other animals were executed and processed with gross anatomy after the end of the observation period. The gross pathologic change of each animal was recorded.

10.3.6 Data Processing

Statistically calculating $LD_{50}$ and confidence limit with bliss software

11. Result and Conclusion 11.1.1 Result

Result of clinical observation 11.1.2 Clinical Symptoms of the 5 Dose Groups are Shown in Attached table 1.

Statistical result of animal death

During the observation period, all of the rats in the dose group 5 died. In the dose group 4, all of the female rats died and 4 male rats died. In the dose group 3, 4 female rats died and no male rat die. In the dose group 2, 2 female rats died and 1 male rat died. In the dose group 1, none of the rats died. The other animals survived, as shown in Attached table 2.

11.1.3 Animal Weight

The animals were weighed once on the dosing day. During the observation period, the animals were weighed once every 3 days, as shown in Attached table 3-4.

11.1.4 Result of Gross Anatomy

The test animals were processed with gross anatomy, wherein 6 animals had a symptom of rough liver surface, as shown in Attached table 5.

11.1.5 Conclusion $LD_{50}$ and confidence limit of the test sample

According to [H] GPT1-1 *Technical guidelines for acute toxicity testing of chemicals* issued by China Food and Drug Administration (CFDA) and results of pre-test, doses were designed and the test were processed. According to the results of the test, median lethal dose ($LD_{50}$) of P13 in this acute oral toxicity testing in male and female SD rats was calculated and listed as follows.

Male rats: 677.58 mg/kg, confidence limit: 449.99~1047 mg/kg Female rats: 379.96 mg/kg, confidence limit: 252.94~564.88 mg/kg 12. File Storage Principal of file management: Zhenyu Nan Telephone: 50793648

After being archived, the following files would be preserved in the archives office of the testing institution for 10 years.

Test plan and its revised sheets

Original record

Final report, etc.

In addition, after the retention test sample was archived, it would be preserved for 5 years or until expiry date.

For extending the retention time, the client should negotiate with the testing institution about the details.

13. Test Deviation

The test was conducted according to Plan F13003 and related SOP, and there was no deviation in the test.

14. Attached Tables

Attached table 1. Result table of clinical symptom

| Symptom | 194 mg/kg kw | 324 mg/kg kw | 540 mg/kg kw | 900 mg/kg kw | 1500 mg/kg kw |
|---|---|---|---|---|---|
| Slow movement | 0 | 0 | 0 | 0 | 2 |
| Low autogenic movement | 0 | 0 | 0 | 0 | 1 |

Attached table 2. Result table of animal death

| Gender | Dose (mg/kg bw) | Deaths/Total number | Death rate (%) |
|---|---|---|---|
| Male | 194 | 0/5 | 0 |
| | 324 | 1/5 | 20 |
| | 540 | 0/5 | 0 |

Attached table 2. Result table of animal death

| Gender | Dose (mg/kg bw) | Deaths/Total number | Death rate (%) |
|---|---|---|---|
| | 900 | 4/5 | 80 |
| | 1500 | 5/5 | 100 |
| Female | 194 | 0/5 | 0 |
| | 324 | 2/5 | 40 |
| | 540 | 4/5 | 80 |
| | 900 | 5/5 | 100 |
| | 1500 | 5/5 | 100 |

Attached table 3.

| Gender | Original code | Weight when grouping (g) | New code |
|---|---|---|---|
| Comparison table of weights of male animals when grouping | | | |
| Male | 110 | 162.12 | 1400 |
| Male | 111 | 168.23 | 1102 |
| Male | 112 | 170.35 | 1302 |
| Male | 113 | 165.37 | 1401 |
| Male | 114 | 174.36 | 1203 |
| Male | 115 | 167.37 | 1501 |
| Male | 116 | 169.52 | 1202 |
| Male | 117 | 175.24 | 1403 |
| Male | 118 | 162.49 | 1500 |
| Male | 119 | 179.48 | 1304 |
| Male | 120 | 174.58 | 1303 |
| Male | 121 | 172.62 | 1502 |
| Male | 122 | 177.37 | 1104 |
| Male | 123 | 173.72 | 1103 |
| Male | 124 | 180.47 | 1404 |
| Male | 125 | 183.57 | — |
| Male | 126 | 170.36 | 1402 |
| Male | 127 | 176.37 | 1503 |
| Male | 128 | 160.36 | 1100 |
| Male | 129 | 163.57 | 1201 |
| Male | 130 | 161.37 | 1300 |
| Male | 131 | 160.37 | 1200 |
| Male | 132 | 180.47 | 1504 |
| Male | 133 | 178.36 | 1204 |
| Male | 134 | 185.37 | — |
| Male | 135 | 164.36 | 1301 |
| Male | 136 | 163.56 | 1101 |
| Comparison table of weights of female animals when grouping | | | |
| Female | 200 | 160.26 | 2402 |
| Female | 201 | 160.36 | 2103 |
| Female | 202 | 157.26 | 2102 |
| Female | 203 | 147.25 | — |
| Female | 204 | 150.37 | — |
| Female | 205 | 160.32 | 2502 |
| Female | 206 | 164.38 | 2204 |
| Female | 207 | 158.24 | 2202 |
| Female | 208 | 160.36 | 2203 |
| Female | 209 | 158.29 | 2302 |
| Female | 210 | 162.47 | 2503 |
| Female | 211 | 160.47 | 2303 |
| Female | 212 | 164.78 | 2304 |
| Female | 213 | 156.93 | 2501 |
| Female | 214 | 161.47 | 2403 |
| Female | 215 | 155.69 | 2101 |
| Female | 216 | 151.68 | 2100 |
| Female | 217 | 155.82 | 2201 |
| Female | 218 | 156.92 | 2401 |
| Female | 219 | 153.83 | 2300 |
| Female | 220 | 164.78 | 2404 |
| Female | 221 | 156.72 | 2301 |
| Female | 222 | 152.17 | 2200 |
| Female | 223 | 155.38 | 2500 |
| Female | 224 | 165.83 | 2504 |
| Female | 225 | 164.29 | 2104 |
| Female | 226 | 154.92 | 2400 |

Attached table 4.

Unit: g

| Dose | Gender | Code | On the dosing day | On the 3rd day after dosing | On the 6th day after dosing | On the 9th day after dosing | On the 12th day after dosing | On the 14th day after dosing |
|---|---|---|---|---|---|---|---|---|
| Change table of weights of male animals | | | | | | | | |
| 194 mg/kg bw | Male | 1100 | 160.36 | 187.25 | 209.11 | 232.71 | 254.51 | 261.54 |
| | Male | 1101 | 163.56 | 199.54 | 224.78 | 248.02 | 271.29 | 290.34 |
| | Male | 1102 | 168.23 | 186.62 | 215.61 | 238.65 | 258.08 | 280.08 |
| | Male | 1103 | 173.72 | 205.92 | 232.43 | 250.42 | 271.87 | 286.79 |
| | Male | 1104 | 177.37 | 197.35 | 220.17 | 248.63 | 268.82 | 283.05 |
| 324 mg/kg bw | Male | 1200 | 160.37 | 176.05 | 189.74 | 216.22 | 233.89 | 243.10 |
| | Male | 1201 | 163.57 | 179.46 | 199.27 | 227.62 | 252.95 | 265.23 |
| | Male | 1202 | 169.52 | 188.08 | 211.98 | 238.04 | 258.78 | 273.71 |
| | Male | 1203 | 174.36 | 185.62 | — | — | — | — |
| | Male | 1204 | 178.36 | 192.57 | 200.03 | 229.32 | 252.63 | 254.23 |
| 540 mg/kg bw | Male | 1300 | 161.37 | 162.56 | 167.38 | 193.05 | 204.22 | 212.49 |
| | Male | 1301 | 164.36 | 175.49 | 186.33 | 216.37 | 238.51 | 252.91 |
| | Male | 1302 | 170.35 | 179.35 | 191.38 | 217.62 | 233.24 | 246.58 |
| | Male | 1303 | 174.58 | 180.04 | 190.46 | 206.82 | 229.40 | 238.19 |
| | Male | 1304 | 179.48 | 184.32 | 200.35 | 221.15 | 245.18 | 256.24 |
| 900 mg/kg bw | Male | 1400 | 162.12 | 163.76 | 171.35 | 189.35 | 205.78 | 220.49 |
| | Male | 1401 | 165.37 | — | — | — | — | — |
| | Male | 1402 | 170.36 | — | — | — | — | — |
| | Male | 1403 | 175.24 | — | — | — | — | — |
| | Male | 1404 | 180.47 | — | — | — | — | — |
| 1500 mg/kg bw | Male | 1500 | 162.49 | — | — | — | — | — |
| | Male | 1501 | 167.37 | — | — | — | — | — |
| | Male | 1502 | 172.62 | — | — | — | — | — |
| | Male | 1503 | 176.37 | — | — | — | — | — |
| | Male | 1504 | 180.47 | — | — | — | — | — |

-continued

Attached table 4.

Unit: g

| Dose | Gender | Code | On the dosing day | On the 3rd day after dosing | On the 6th day after dosing | On the 9th day after dosing | On the 12th day after dosing | On the 14th day after dosing |
|---|---|---|---|---|---|---|---|---|
| Change table of weights of female animals | | | | | | | | |
| 194 mg/kg bw | Female | 2100 | 151.68 | 165.35 | 166.65 | 185.08 | 192.48 | 190.81 |
| | Female | 2101 | 155.69 | 168.30 | 173.09 | 190.37 | 192.87 | 200.02 |
| | Female | 2102 | 157.26 | 171.42 | 180.83 | 193.52 | 191.41 | 204.56 |
| | Female | 2103 | 160.36 | 172.62 | 178.38 | 202.38 | 203.01 | 205.79 |
| | Female | 2104 | 164.29 | 174.31 | 178.67 | 199.36 | 200.18 | 200.19 |
| 324 mg/kg bw | Female | 2200 | 152.17 | 162.45 | 161.46 | 171.42 | 181.76 | 188.53 |
| | Female | 2201 | 155.82 | — | — | — | — | — |
| | Female | 2202 | 158.24 | 161.63 | 165.92 | 184.92 | 186.81 | 195.31 |
| | Female | 2203 | 160.36 | 170.92 | 178.83 | 197.82 | 199.21 | 214.08 |
| | Female | 2204 | 164.38 | — | — | — | — | — |
| 540 mg/kg bw | Female | 2300 | 153.83 | — | — | — | — | — |
| | Female | 2301 | 156.72 | — | — | — | — | — |
| | Female | 2302 | 158.29 | 160.58 | 175.35 | 187.71 | 197.17 | 208.85 |
| | Female | 2303 | 160.47 | — | — | — | — | — |
| | Female | 2304 | 164.78 | — | — | — | — | — |
| 900 mg/kg bw | Female | 2400 | 154.92 | — | — | — | — | — |
| | Female | 2401 | 156.92 | — | — | — | — | — |
| | Female | 2402 | 160.26 | — | — | — | — | — |
| | Female | 2403 | 161.47 | — | — | — | — | — |
| | Female | 2404 | 164.78 | — | — | — | — | — |
| 1500 mg/kg bw | Female | 2500 | 155.38 | — | — | — | — | — |
| | Female | 2501 | 156.93 | — | — | — | — | — |
| | Female | 2502 | 160.32 | — | — | — | — | — |
| | Female | 2503 | 162.47 | — | — | — | — | — |
| | Female | 2504 | 165.83 | — | — | — | — | — |

Attached table 5.

| Animal code | Gender | Death type | Visceral organ | Gross anatomy result |
|---|---|---|---|---|
| Result table of gross anatomy of male animals | | | | |
| 1100 | Male | Planned anatomy | All | No macroscopic abnormality |
| 1101 | Male | Planned anatomy | All | No macroscopic abnormality |
| 1102 | Male | Planned anatomy | All | No macroscopic abnormality |
| 1103 | Male | Planned anatomy | All | No macroscopic abnormality |
| 1104 | Male | Planned anatomy | All | No macroscopic abnormality |
| 1200 | Male | Planned anatomy | All | No macroscopic abnormality |
| 1201 | Male | Planned anatomy | All | No macroscopic abnormality |
| 1202 | Male | Planned anatomy | All | No macroscopic abnormality |
| 1203 | Male | Unplanned anatomy | All | No macroscopic abnormality |
| 1204 | Male | Planned anatomy | All | No macroscopic abnormality |
| 1300 | Male | Planned anatomy | All | No macroscopic abnormality |
| 1301 | Male | Planned anatomy | All | Rough liver surface |
| 1302 | Male | Planned anatomy | All | Rough liver surface |
| 1303 | Male | Planned anatomy | All | No macroscopic abnormality |
| 1304 | Male | Planned anatomy | All | No macroscopic abnormality |
| 1400 | Male | Planned anatomy | All | No macroscopic abnormality |
| 1401 | Male | Unplanned anatomy | All | No macroscopic abnormality |
| 1402 | Male | Unplanned anatomy | All | No macroscopic abnormality |
| 1403 | Male | Unplanned anatomy | All | No macroscopic abnormality |
| 1404 | Male | Unplanned anatomy | All | No macroscopic abnormality |
| 1500 | Male | Unplanned anatomy | All | No macroscopic abnormality |
| 1501 | Male | Unplanned anatomy | All | No macroscopic abnormality |
| 1502 | Male | Unplanned anatomy | All | No macroscopic abnormality |
| 1503 | Male | Unplanned anatomy | All | No macroscopic abnormality |
| 1504 | Male | Unplanned anatomy | All | No macroscopic abnormality |
| Result table of gross anatomy of female animals | | | | |
| 2100 | Female | Planned anatomy | All | No macroscopic abnormality |
| 2101 | Female | Planned anatomy | All | No macroscopic abnormality |
| 2102 | Female | Planned anatomy | All | No macroscopic abnormality |
| 2103 | Female | Planned anatomy | All | No macroscopic abnormality |
| 2104 | Female | Planned anatomy | All | No macroscopic abnormality |
| 2200 | Female | Planned anatomy | All | No macroscopic abnormality |
| 2201 | Female | Unplanned anatomy | All | No macroscopic abnormality |
| 2202 | Female | Planned anatomy | All | Rough liver surface |

-continued

Attached table 5.

| Animal code | Gender | Death type | Visceral organ | Gross anatomy result |
|---|---|---|---|---|
| 2203 | Female | Planned anatomy | All | Rough liver surface |
| 2204 | Female | Unplanned anatomy | All | No macroscopic abnormality |
| 2300 | Female | Unplanned anatomy | All | No macroscopic abnormality |
| 2301 | Female | Unplanned anatomy | All | No macroscopic abnormality |
| 2302 | Female | Planned anatomy | All | Rough liver surface |
| 2303 | Female | Unplanned anatomy | All | No macroscopic abnormality |
| 2304 | Female | Unplanned anatomy | All | No macroscopic abnormality |
| 2400 | Female | Unplanned anatomy | All | No macroscopic abnormality |
| 2401 | Female | Unplanned anatomy | All | No macroscopic abnormality |
| 2402 | Female | Unplanned anatomy | All | No macroscopic abnormality |
| 2403 | Female | Unplanned anatomy | All | No macroscopic abnormality |
| 2404 | Female | Unplanned anatomy | All | No macroscopic abnormality |
| 1500 | Female | Unplanned anatomy | All | No macroscopic abnormality |
| 1501 | Female | Unplanned anatomy | All | No macroscopic abnormality |
| 1502 | Female | Unplanned anatomy | All | No macroscopic abnormality |
| 1503 | Female | Unplanned anatomy | All | No macroscopic abnormality |
| 1504 | Female | Unplanned anatomy | All | No macroscopic abnormality |
| 2500 | Female | Unplanned anatomy | All | No macroscopic abnormality |
| 2501 | Female | Unplanned anatomy | All | No macroscopic abnormality |
| 2502 | Female | Unplanned anatomy | All | No macroscopic abnormality |
| 2503 | Female | Unplanned anatomy | All | No macroscopic abnormality |
| 2504 | Female | Unplanned anatomy | All | No macroscopic abnormality |

What is claimed is:

1. A resveratrol selenide, having a structure of:

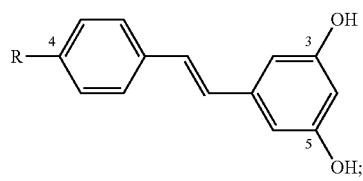

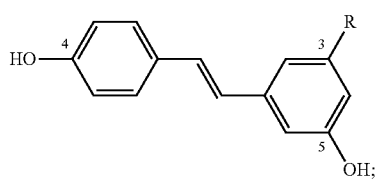

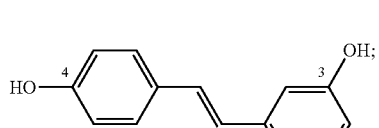

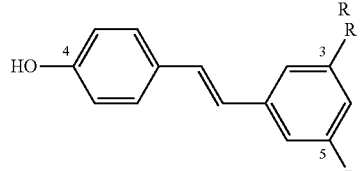

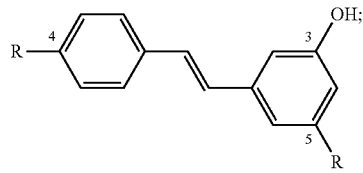

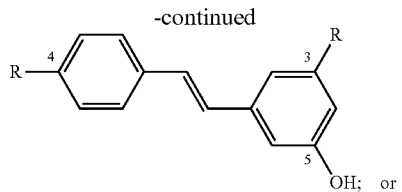

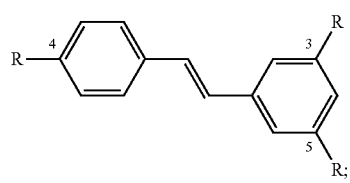

wherein

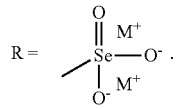

2. A method for preparing the resveratrol selenide, as recited in claim 1, comprising following steps of:
(a) reacting trans-resveratrol with at least one inorganic metallic alkali, to obtain resveratrol hydroxy acid salt; and
(b) reacting the resveratrol hydroxy acid salt with $SeO_2$, to obtain preparation of the trans-resveratrol selenide, which has a functional group of

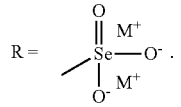

3. The method for preparing the resveratrol selenide, as recited in claim 2, wherein the inorganic metallic alkali in step (a) is sodium hydroxide, potassium hydroxide, or magnesium hydroxide.

4. The method for preparing the resveratrol selenide, as recited in claim 2, wherein a reaction temperature in step (a) is 80° C.-150° C., and a reaction temperature in step (b) is 120° C.-360° C.

5. The method for preparing the resveratrol selenide, as recited in claim 2, wherein a purity of the trans-resveratrol in step (a) is not less than 99%.

6. The method for preparing the resveratrol selenide, as recited in claim 2, wherein preparation of the trans-resveratrol selenide obtained in step (b), which has the functional group of

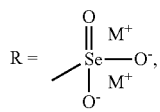

comprises trans-resveratrol selenide accounting for not less than 80% (mass fraction), cis-resveratrol selenide accounting for not more than 8%, and highly purified resveratrol accounting for not less than 10%, wherein a purity of the highly purified resveratrol is not less than 99%.

* * * * *